(12) United States Patent
Baker

(10) Patent No.: US 9,541,494 B2
(45) Date of Patent: Jan. 10, 2017

(54) APPARATUS AND METHOD TO MEASURE DISPLAY QUALITY

(71) Applicant: Tektronix, Inc., Beaverton, OR (US)

(72) Inventor: Daniel G. Baker, Beaverton, OR (US)

(73) Assignee: TEKTRONIX, INC., Beaverton, OR (US)

( * ) Notice: Subject to any disclaimer, the term of this patent is extended or adjusted under 35 U.S.C. 154(b) by 423 days.

(21) Appl. No.: 14/133,470

(22) Filed: Dec. 18, 2013

(65) Prior Publication Data

US 2015/0168293 A1    Jun. 18, 2015

(51) Int. Cl.
| | |
|---|---|
| *G06F 11/30* | (2006.01) |
| *G01N 21/25* | (2006.01) |
| *G01J 1/42* | (2006.01) |
| *H04N 17/04* | (2006.01) |
| *H04N 13/04* | (2006.01) |

(52) U.S. Cl.
CPC ............. *G01N 21/251* (2013.01); *G01J 1/42* (2013.01); *G01N 21/25* (2013.01); *H04N 13/04* (2013.01); *H04N 13/0422* (2013.01); *H04N 13/0425* (2013.01); *H04N 17/04* (2013.01)

(58) Field of Classification Search
CPC ............. G09G 2320/0233; G09G 2320/0242; G09G 2320/062; G09G 2320/0626; G09G 2320/0693; G09G 2330/021; G09G 2360/14; G09G 2360/144; G09G 2360/145; G09G 3/2092; G09G 3/3466; G09G 3/3611; G09G 2300/08

See application file for complete search history.

(56) References Cited

U.S. PATENT DOCUMENTS

| | | |
|---|---|---|
| 5,050,989 A | 9/1991 | Van Tassel et al. |
| 6,950,495 B2 | 9/2005 | Nelson et al. |
| 2005/0068466 A1 | 3/2005 | Waters et al. |

(Continued)

OTHER PUBLICATIONS

European Patent Office, Extended European Search Report, Application No. 14198957.4, Jun. 8, 2015, 6 pages, Munich, Germany.

(Continued)

*Primary Examiner* — Roy Y Yi
(74) *Attorney, Agent, or Firm* — Andrew J. Harrington; Marger Johnson

(57) ABSTRACT

A method for measuring a quality parameter, such as luminance uniformity, of a video display, according to some embodiments of the present invention, includes providing a plurality of pattern images to be displayed sequentially on the video display, measuring the amount of light produced by each pattern image using a wide-angle light sensor, and calculating the video display quality parameter using the measured light values corresponding to each displayed pattern. Each pattern used in accordance with this method is derived from an orthogonal matrix, resulting in each pattern having a high average brightness, thereby eliminating the need to use a narrow-angle, spot light meter, and instead allowing measurements to be made using a simple, wide-angle, incident-light or reflected-light photometer. This method is compliant with the relevant SMPTE measurement standard for measuring luminance uniformity. Additionally, some embodiments of the present invention provide an apparatus for practicing this method.

24 Claims, 8 Drawing Sheets

(56) References Cited

U.S. PATENT DOCUMENTS

| | | | |
|---|---|---|---|
| 2008/0079852 A1* | 4/2008 | Nagaishi | G09G 3/36 |
| | | | 348/739 |
| 2010/0020201 A1* | 1/2010 | Chao | G06T 3/4038 |
| | | | 348/239 |
| 2010/0158481 A1* | 6/2010 | Kaneko | G11B 27/105 |
| | | | 386/241 |
| 2011/0216390 A1* | 9/2011 | Tong | G02B 27/48 |
| | | | 359/279 |
| 2012/0262556 A1 | 10/2012 | Kuwahara et al. | |

OTHER PUBLICATIONS

Sloane & Harwit, Masks for Hadamard Transform Optics, and Weighing Designs, Applied Optics, Jan. 1976, 107-14, vol. 15—No. 1, Optical Society of America, Washington, DC, USA.

Koukouvinos & Seberry, Weighing Matrices and Their Applications, Journal of Statistical Planning and Inference, 1997, No. 62, 91-101, Elsevier, B.V., Amsterdam, N. L. (available at http://www.uow.edu.au/~jennie/WEBPDF/1997_05.pdf).

Spectra Cine, Inc., Spectra Cinespot One-Degree Spotmeter, http://www.spectracine.com/Product_3.html, 2005, Spectra Cine, Inc., Burbank, CA, USA (last visited Dec. 10, 2013).

* cited by examiner

APPARATUS AND METHOD TO MEASURE DISPLAY QUALITY

FIELD OF THE INVENTION

The present invention relates to measuring the quality of video displays, and particularly to measuring a display's brightness or luminance uniformity.

BACKGROUND OF THE INVENTION

One important measure of the quality of a video display, including flat panel displays and cinema projection screens, is the uniformity of brightness, or luminance. With respect to cinema projection screens, in order to maintain an optimal viewing experience, cinema operators must periodically perform a measurement of the consistency of luminance across the screen in both the horizontal and vertical dimensions. Both the cinema screen itself and the video projection system can contribute to luminance non-uniformity. Over time, a screen can become dirty or damaged, creating the appearance of "dark" or "light" spots on the screen. These dirty or damaged spots can be colored so as to only affect certain colors of light, thereby creating a color-cast across the screen. Even on a clean and well-maintained screen, the distance of the projector from the screen and the type of lens used on the projector can cause areas of illumination non-uniformity. Additionally, a cinema's ambient lighting may create areas of inconsistent screen illumination.

Various industry organizations prescribe standards for measuring a cinema screen's luminance uniformity. Both the American National Standards Institute (ANSI) and the Society of Motion Picture and Television Engineers (SMPTE) standards specify measuring a screen's brightness in each of nine zones, wherein each zone is defined by dividing the screen into a 3×3 grid consisting of nine equally sized rectangles. For example, see SMPTE RP98-1995 (hereinafter "the relevant measurement standard," "the relevant SMPTE standard," or simply "the relevant standard"), which states that "the screen is considered to be divided into nine equal-size rectangles." The standard further specifies that a luminance measurement for each of these nine zones is to be made from six different measurement locations within the theater: the left edge seat, right edge seat, and center seat of the center row of the theater, and the left edge seat, right edge seat, and center seat of the rear row of the theater. At each measurement location (seat) within the theater, the nine measured luminance values are recorded and the screen is determined to be within specification if the measured luminance of center zone of the screen is within specified absolute limits (e.g. "between 12 fL and 22 fL"), and if the measured luminance of the remaining 8 zones of the screen are within specified limits relative to the center zone (e.g. "luminance of the screen sides and corners shall be at least 80% of the screen center reading"), as well as relative to each other (e.g. "the remaining eight measurement points shall not differ by more than 4 fL").

Each measurement is typically made using a spot light meter, such as the Spectra Cinespot One-Degree Spotmeter (see http://www.spectracine.com/Product_3.html), by displaying a flat field (all white) frame on the screen, then sequentially pointing the spot light meter at the center of each of the nine zones of the screen and recording the light value measured by the meter. Because these types of spot light meters have narrow view-angle lenses, the meter only "sees" a small area of the screen, and thus measures the reflected light only from the particular zone being measured. A spot light meter suitable to make such a measurement can be significantly expensive.

An alternative to using a spot light meter would be to use a simple, lower-cost, wide-angle reflected light meter or wide-angle incident light meter. Because a wide-angle meter "sees" the entire screen, and not just the particular zone being measured, a wide-angle meter would need to be used in conjunction with a sequence of patterns that could be displayed on the screen, where each pattern illuminated only one of the nine measurement zones. However, the wide-angle meter would be required to have a high dynamic range to be capable of measuring these relatively low light levels (one-ninth of full screen brightness). A high dynamic range would make the required wide-angle light meter more expensive. Also, the ambient light in the theater would need to be substantially reduced in order to avoid contaminating these low light level measurements. Reducing the ambient light to an acceptable level could be impractical or inconvenient in many cases.

Furthermore, regardless of whether a spot light meter or a wide-angle meter is used, the measurement process described above requires at least 54 separate manual measurements (1 measurement per measurement zone times 9 zones per measurement location times 6 measurement locations), which can be tedious and prone to error.

What is needed is a method and apparatus of measuring a screen's brightness uniformity that does not require reduction of the ambient light in the theater, and that allows the use of a simple, wide-angle light meter without a large dynamic range, such as a typical photocell light meter, or a photocell incorporated into a typical modern mobile phone's camera.

SUMMARY OF THE INVENTION

A method for measuring a quality parameter, such as luminance uniformity, of a video display, according to some embodiments of the present invention, includes providing a plurality of pattern images to be displayed sequentially on the video display, measuring the amount of light produced by each pattern image using a wide-angle light sensor, and calculating the video display quality parameter using the measured light values corresponding to each displayed pattern. Each pattern used in accordance with this method is derived from an orthogonal matrix, resulting in each pattern having a high average brightness, thereby eliminating the need to use a narrow-angle, spot light meter, and instead allowing measurements to be made using a simple, wide-angle, incident-light or reflected-light photometer. This method is compliant with the relevant SMPTE measurement standard for measuring luminance uniformity. Additionally, some embodiments of the present invention provide an apparatus for practicing this method.

One feature of the present invention is the plurality of patterns to be displayed on the screen. The composition of each pattern is important to successfully achieve the desired measurement. Each individual pattern may be referred to as a "mask pattern." Each mask pattern is a two-dimensional image comprised of equally-sized rectangles, wherein each rectangle may be illuminated to one of two selected intensity levels. Within each mask pattern, approximately half of the rectangles are illuminated to one intensity level, and the remaining rectangles are illuminated to the other intensity level. Therefore, each mask pattern, when displayed, produces about the same total luminance output (approximately one-half of full screen luminance). Thus, these mask patterns do not require the light sensor to have a high dynamic range, and do not require the user to reduce the ambient light. Derivation of these mask patterns is described in more detail below.

By changing the type of wide-angle light sensors used, or the mask patterns used, or both, variations of this method and apparatus can also be used to measure other quality parameters of a display screen including chrominance uniformity, grayscale uniformity, and stereoscopic 3D crosstalk uniformity.

The objects, advantages, and other novel features of the present invention are apparent from the following detailed description when read in conjunction with the appended claims and attached drawings.

DETAILED DESCRIPTION OF THE INVENTION

Figure 1:
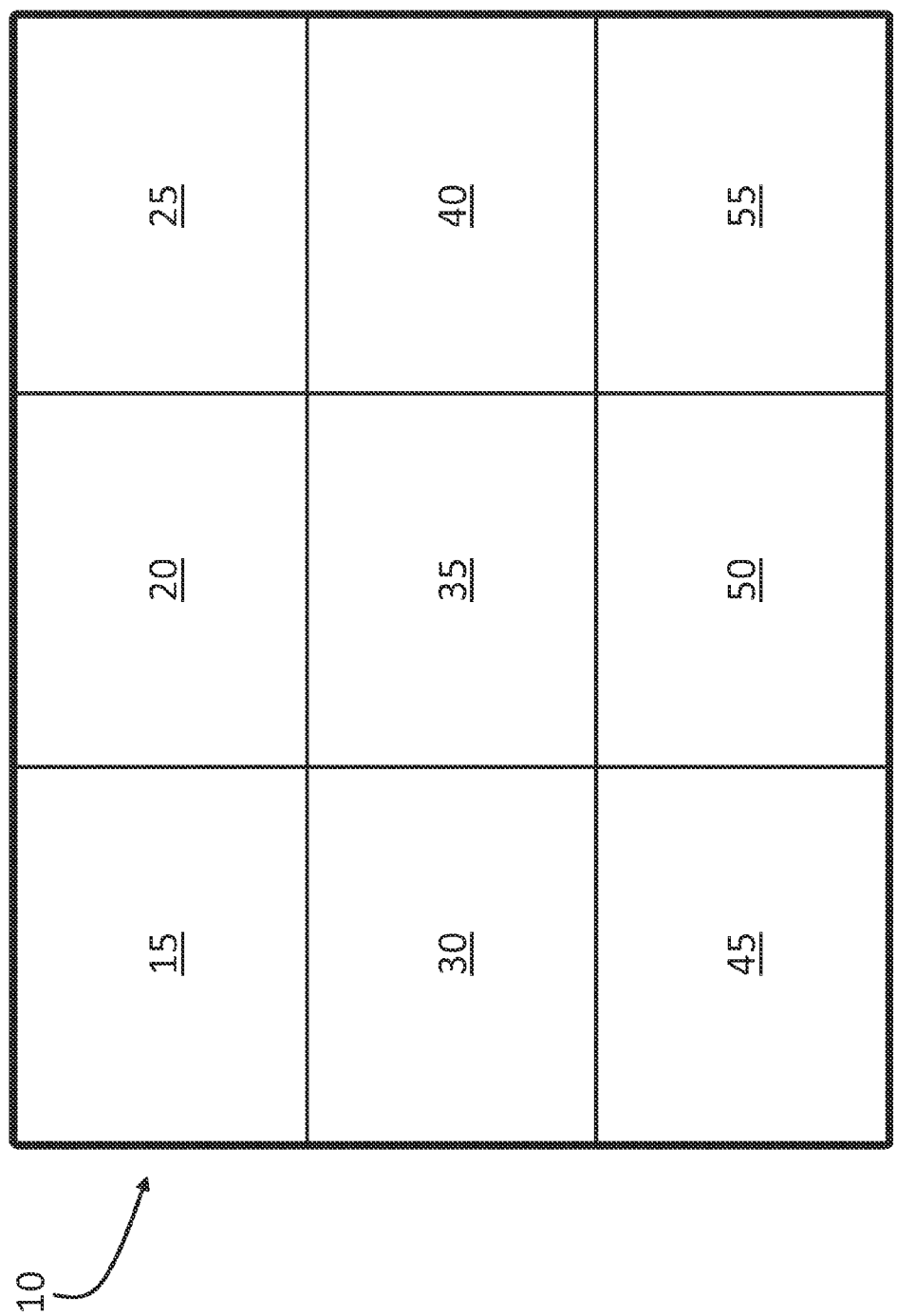
FIG. 1 depicts a video display screen divided into measurement zones, according to a conventional method of measuring luminance uniformity.

FIG. 1 shows a prior art video display screen 10 logically divided into nine equally sized rectangles (shown by thinner lines) that define the nine measurement zones required by the relevant SMPTE measurement standard. Each zone may be referred to by a name corresponding to the zone's row and column position on the screen, from the perspective of a person viewing the screen. For example, the four "corner" zones 15, 25, 45, and 55 may be referred to, respectively, as the "top-left," "top-right," "bottom-left," and "bottom-right" zones. The four "edge" zones 20, 30, 40, and 50 may be referred to, respectively, as the "top-center," "center-left," "center-right," and "bottom-center" zones. Zone 35 may be referred to as the "center" zone.

Figure 2:
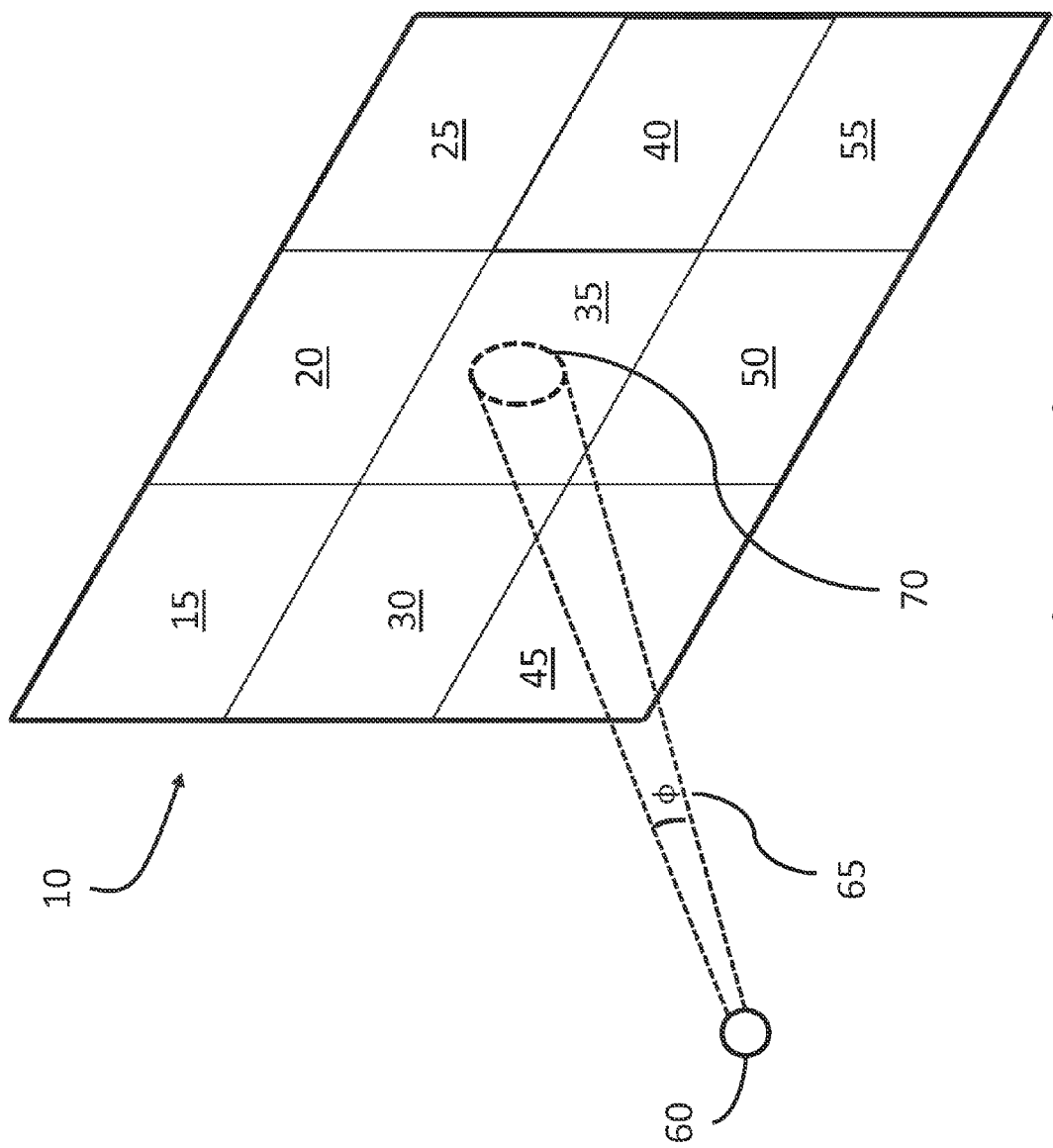
FIG. 2 illustrates a spot light meter being used to measure luminance in one of the measurement zones of a video display screen according to a conventional method of measuring luminance uniformity.

FIG. 2 shows a perspective view of a spot light meter 60 being used to measure luminance of the display 10 of FIG. 1 according to a conventional method. A full brightness (all white) image is displayed on the screen 10. From a selected viewing location, the spot light meter 60 is aimed at the approximate center of one of the measurement zones on the screen 10 and a luminance measurement is recorded for that zone. For example, in FIG. 2, the spot light meter 60 is aimed at the approximate center of the center zone 35. The viewing location may be selected as a typical viewer's distance from the screen, or, in the case of a cinema screen, may be selected according to the relevant measurement specifications, for example, the relevant SMPTE specification's six required seat locations. Because the spot light meter 60 has a relatively narrow viewing angle 65, the spot light meter 60 measures the luminance of only a relatively small area 70 of the screen 10. A user (not shown) proceeds to aim the spot light meter 60 at the center of each of the other measurement zones 15, 20, 25, 30, 40, 45, 50, and 55, and records luminance measurements for each zone. The user then calculates the screen's luminance uniformity at the selected viewing location using the recorded measurements. The user then repeats the luminance measurements and luminance uniformity calculations from any other desired viewing locations. A complete set of measurements according to the relevant SMPTE specification requires at least 54 separate brightness measurements: nine at each viewing location times six viewing locations in a theater.

Figure 3:
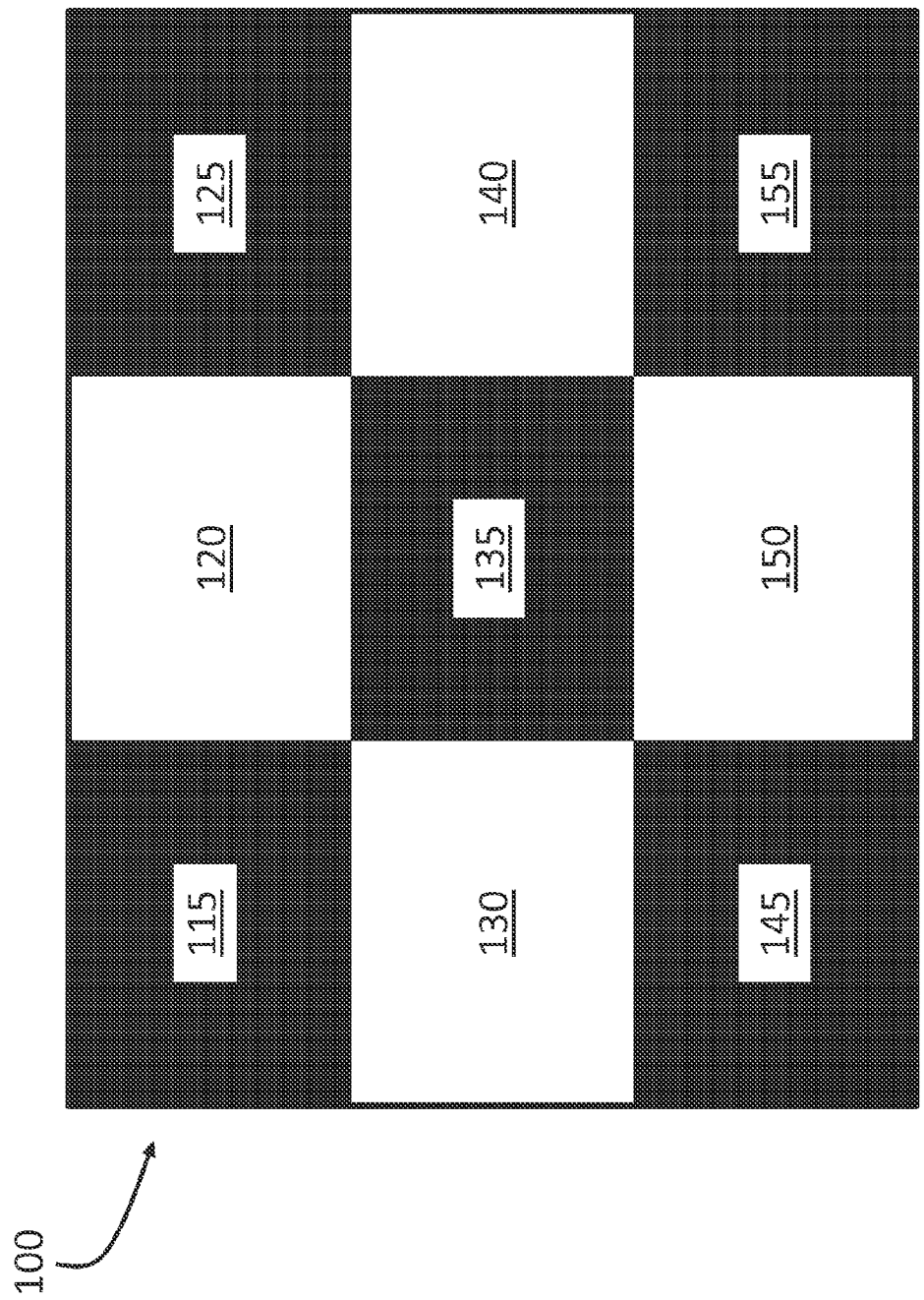
FIG. 3 depicts a mask pattern according to some embodiments of the present invention.

FIG. 3 shows an example of a mask pattern 100 that is, according to some embodiments of the present invention, to be displayed on a display screen and used in conjunction with other mask patterns in a set of mask patterns, to measure a quality parameter of the screen. The mask pattern 100 shown in FIG. 3 comprises nine equally sized rectangular areas 115, 120, 125, 130, 135, 140, 145, 150, and 155. When a displayed mask pattern fills the screen, these rectangular areas have the same boundaries as the nine measurement zones shown in FIG. 1. These rectangular areas may also be referred to as "patches" of the screen. Each patch in a mask pattern is illuminated with one of two selected colors of light at one of two selected intensity levels. The two selected colors of light may be the same, that is, the first selected color of light and the second selected color of light may both be, for example, white light. In the example mask pattern 100 shown in FIG. 3, each rectangle is illuminated with white light to either zero intensity (black) or full intensity (white). One of ordinary skill in the art will appreciate that the first and second selected intensities of light do not need to be 0% and 100%, respectively, but rather could be, for example, 10% and 90%, respectively. The mask pattern shown in FIG. 3 contains four white patches 120, 130, 140, and 150, and five black patches 115, 125, 135, 145, 155. Thus, when displayed on screen, mask pattern 100 produces approximately one-half (four-ninths) the luminance output relative to full-screen luminance (i.e. the total luminance output produced if all nine patches were white).

Figure 4A:
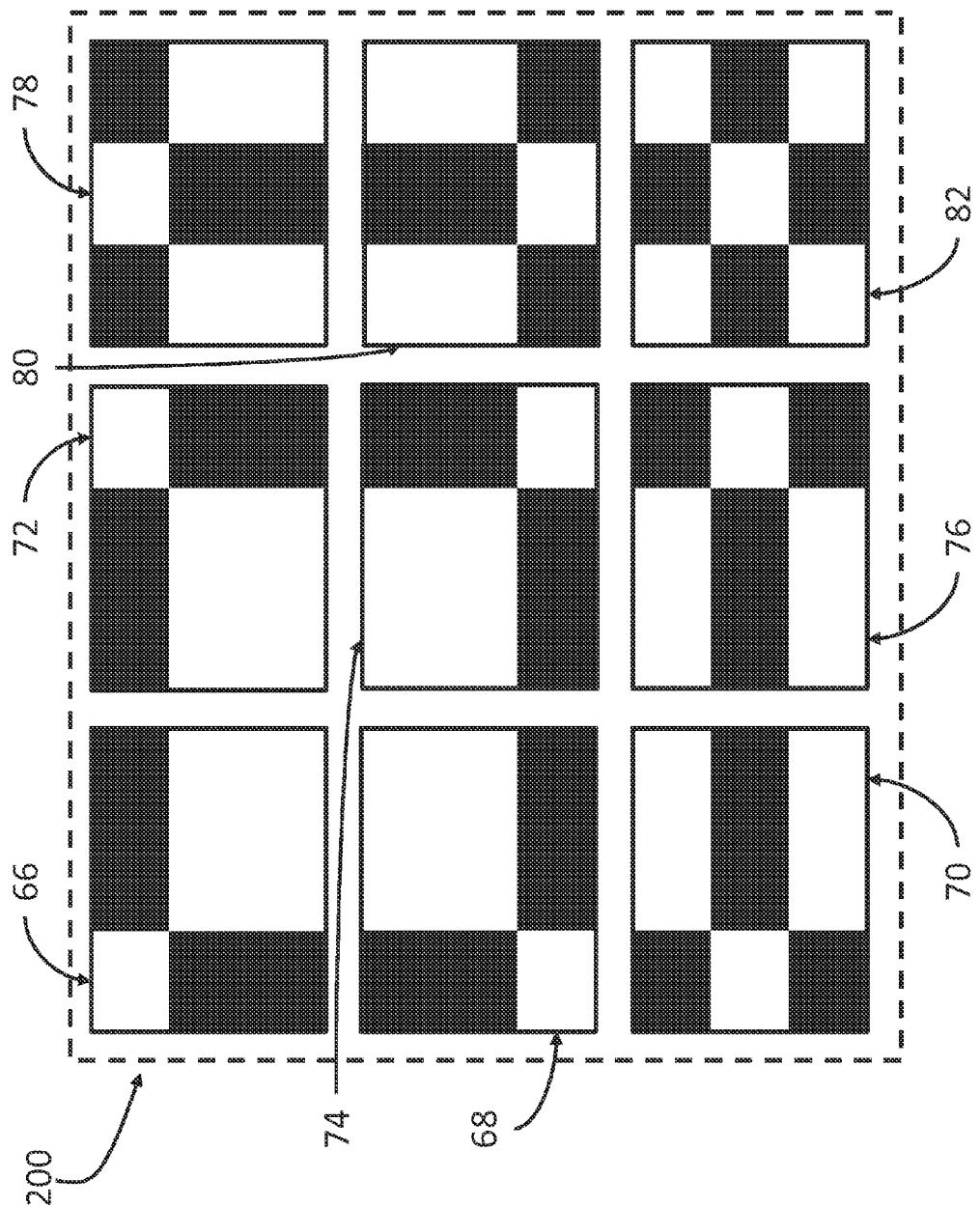
FIG. 4A depicts a set of nine mask patterns according to some embodiments of the present invention.

FIG. 4A shows a set of mask patterns 200 comprising nine individual mask patterns 66, 68, 70, 72, 74, 76, 78, 80, and 82 that, according to some embodiments of the present invention, may be displayed in sequence on a display screen and used to measure the screen's luminance uniformity. Each of the mask patterns 66, 68, 70, 72, 74, 76, 78, 80, and 82 contain approximately five white patches and four black patches. Therefore, similar to the mask pattern 100 shown in FIG. 3, each of the mask patterns 66, 68, 70, 72, 74, 76, 78, 80, and 82 in mask pattern set 200 also produces approximately one-half (five-ninths) the luminance output relative to full-screen luminance when displayed on screen. The significance of the particular mask patterns is explained in further detail below.

Figure 4B:
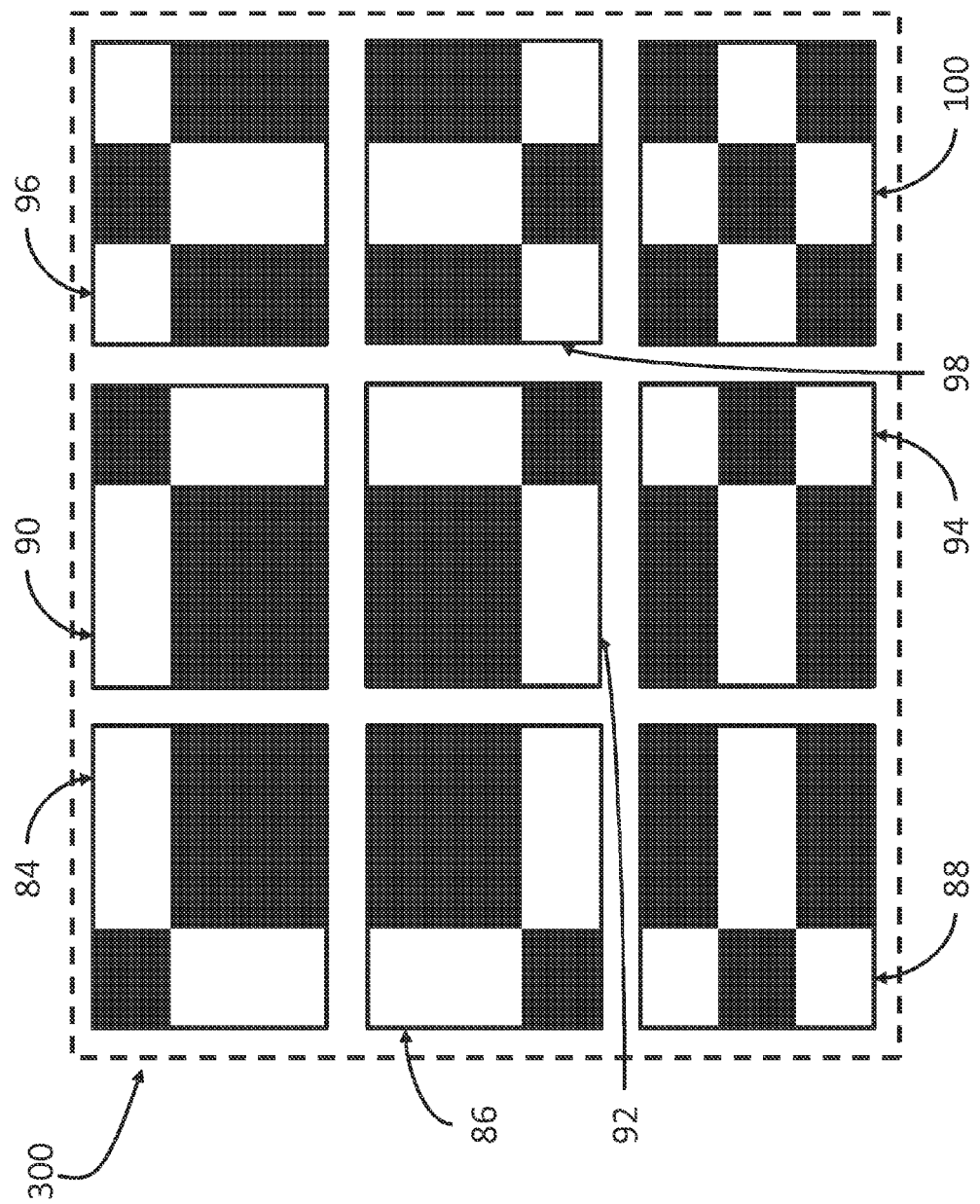
FIG. 4B depicts a set of nine mask patterns that are complementary to the set of mask patterns shown in FIG. 4A, according to some embodiments of the present invention.

FIG. 4B shows a set of mask patterns 300 comprising nine individual mask patterns 84, 86, 88, 90, 92, 94, 96, 98, and 100, that is "complementary" to the mask pattern set 200 shown in FIG. 4A. The mask pattern sets shown in FIG. 4A and FIG. 4B are complementary sets because each mask pattern within one set has a "complementary" mask pattern in the corresponding position within the other set. A mask pattern is complementary to another mask pattern when all of the patches within the second mask pattern are illuminated to the opposite intensity levels as the corresponding patches in the first mask pattern, i.e. all the white patches in the first mask pattern are black in the second mask pattern and all the black patches in the first mask pattern are white in the second mask pattern. For example, mask pattern 100 in mask pattern set 300 shown in FIG. 4B is complementary to mask pattern 82 in mask pattern set 200 shown in FIG. 4A.

To simplify the calculation of a display quality parameter, as described in more detail below, the mask pattern sets 200 and 300 are preferably displayed in sequence, starting (as shown in FIG. 4A and FIG. 4B, respectively) with the "upper-left" mask pattern of the set, 66 and 84, respectively, proceeding from top to bottom through the mask patterns in the leftmost column, then proceeding from top to bottom through the mask patterns in the center column, then proceeding from top to bottom through the mask patterns shown in the rightmost column, ending with the "bottom-right" mask pattern of the set, 82 and 100, respectively. Additionally, to simplify the calculation of a display quality parameter, preferably mask pattern set 200 shown in FIG. 4A should be displayed first, followed by mask pattern set 300 shown in FIG. 4B. However, those skilled in the art will appreciate that the mask patterns could be displayed in other sequences, provided the vectors of measured values corresponding to each mask pattern (discussed below) are rearranged accordingly.

An important feature of the present invention is that the sets of mask patterns are derived from an orthogonal matrix. According to some embodiments of the present invention, the mask patterns are derived from a Walsh-Hadamard matrix. Walsh-Hadamard matrices are well-known orthogonal matrices central to many digital communication standards in which, like all orthogonal matrices, the rows of the matrix are pairwise orthogonal (that is, their inner product or dot product equals zero), and the columns of the matrix are also pairwise orthogonal. Although in the examples discussed below the mask patterns are all derived from Walsh-Hadamard matrices, those skilled in the art will recognize that other types of orthogonal matrices, such as Sylvester matrices, could also be used to derive suitable mask patterns. For the purposes of the present invention, the definition of an "orthogonal matrix" does not require the rows to be orthogonal unit vectors. An orthogonal matrix in the context of the present invention need not have its rows normalized. A matrix's inverse and transpose need not be equal, but rather related by a scalar coefficient, to be defined as an "orthogonal matrix" for the purposes of the present invention.

According to some embodiments of the present invention, the sets of mask patterns used are derived directly from a 4×4 Walsh-Hadamard matrix, by performing the pairwise vector multiplication of each column of the matrix by each row of the matrix. For an orthogonal matrix with dimensions of m rows by n columns, this pairwise vector multiplication results in a set of m×n matrices, wherein each matrix in the set is a pairwise orthogonal matrix of m rows by n columns. For example, starting with a 4×4 Walsh-Hadamard matrix, performing the pairwise vector multiplication of each column of the matrix by each row of the matrix results in a set of 16 4×4 mutually orthogonal matrices (i.e. the dot product of the elements of any matrix pair is zero). This set of 16 matrices is converted to a set of 16 mask patterns by first replacing all the −1 elements with 0's, then by considering an element of a matrix to represent the patch of a mask pattern corresponding to the position of that element in the matrix, and illuminating that patch to white (full intensity) if the corresponding element equals one, or to black (zero intensity) if the corresponding element equals zero.

According to other embodiments of the present invention, the sets of mask patterns used are derived indirectly from a 4×4 Walsh-Hadamard matrix of rank four, by first removing the first row and first column to create a reduced rank symmetric 3×3 matrix of rank three, then performing the pairwise vector multiplication of each column of this 3×3 matrix with each row of this 3×3 matrix to produce a set of nine 3×3 matrices with "quasi-orthogonal" rows (i.e. the dot product of pairwise rows is −1 rather than zero). This set of nine matrices may be referred to as the "basis matrices." Next, two sets of nine matrices, which may be referred to as "binary basis matrices," or simply "binary matrices," are formed from these nine basis matrices. The first set of nine binary matrices is formed by taking the nine basis matrices and replacing the −1's with 0's. The second set of nine binary matrices is formed by taking the nine basis matrices and replacing the −1's with 1's and the 1's with 0's. Finally, these two sets of nine binary matrices are used to generate the two complementary sets of nine mask patterns 200 and 300 shown in FIGS. 4A and 4B, respectively, by considering an element of a binary matrix to represent the patch of a mask pattern corresponding to the position of that element in the binary matrix, and illuminating that patch to white (full intensity) if the corresponding element equals one, or to black (zero intensity) if the corresponding element equals zero.

To further illustrate the derivation of sets of mask patterns, consider starting with the following 4×4 Walsh-Hadamard matrix H:

$$H = \begin{bmatrix} 1 & 1 & 1 & 1 \\ 1 & 1 & -1 & -1 \\ 1 & -1 & 1 & -1 \\ 1 & -1 & -1 & 1 \end{bmatrix}$$

Removing the first row and first column of this 4×4 matrix H creates the following reduced rank symmetric 3×3 matrix G:

$$G = \begin{bmatrix} 1 & -1 & -1 \\ -1 & -1 & 1 \\ -1 & 1 & -1 \end{bmatrix}$$

Pairwise multiplying each column of matrix G by each row of matrix G produces the set of nine 3×3 basis matrices $A_{i,j}$:

$A_{i,j}$ = column $i$ of $G$ · row $j$ of $G$ where i=1 ... 3, j=1 ... 3

Thus, the nine 3×3 basis matrices, $A_{i,j}$, are:

$$A_{1,1} = \begin{bmatrix} 1 & -1 & -1 \\ -1 & 1 & 1 \\ -1 & 1 & 1 \end{bmatrix} A_{1,2} = \begin{bmatrix} -1 & -1 & 1 \\ 1 & 1 & -1 \\ 1 & 1 & -1 \end{bmatrix} A_{1,3} = \begin{bmatrix} -1 & 1 & -1 \\ 1 & -1 & 1 \\ 1 & -1 & 1 \end{bmatrix}$$

-continued $$A_{2,1} = \begin{bmatrix} -1 & 1 & 1 \\ -1 & 1 & 1 \\ 1 & -1 & -1 \end{bmatrix} A_{2,2} = \begin{bmatrix} 1 & 1 & -1 \\ 1 & 1 & -1 \\ -1 & -1 & 1 \end{bmatrix} A_{2,3} = \begin{bmatrix} 1 & -1 & 1 \\ 1 & -1 & 1 \\ -1 & 1 & -1 \end{bmatrix}$$

$$A_{3,1} = \begin{bmatrix} -1 & 1 & 1 \\ 1 & -1 & -1 \\ -1 & 1 & 1 \end{bmatrix} A_{3,2} = \begin{bmatrix} 1 & 1 & -1 \\ -1 & -1 & 1 \\ 1 & 1 & -1 \end{bmatrix} A_{3,3} = \begin{bmatrix} 1 & -1 & 1 \\ -1 & 1 & -1 \\ 1 & -1 & 1 \end{bmatrix}$$

Next, the first set of nine binary matrices is formed by replacing the −1's with 0's in each of the basis matrices. Alternatively, this operation can be described mathematically through the following equation, producing the first set of binary matrices, $$B1_{i,j} = \left( \begin{bmatrix} 1 & 1 & 1 \\ 1 & 1 & 1 \\ 1 & 1 & 1 \end{bmatrix} + A_{i,j} \right) \cdot \frac{1}{2}$$

where $i = 1 \ldots 3, j = 1 \ldots 3$

Thus, the first set of binary matrices, $B1_{i,j}$, are:

$$B1_{1,1} = \begin{bmatrix} 1 & 0 & 0 \\ 0 & 1 & 1 \\ 0 & 1 & 1 \end{bmatrix} B1_{1,2} = \begin{bmatrix} 0 & 0 & 1 \\ 1 & 1 & 0 \\ 1 & 1 & 0 \end{bmatrix} B1_{1,3} = \begin{bmatrix} 0 & 1 & 0 \\ 1 & 0 & 1 \\ 1 & 0 & 1 \end{bmatrix}$$

$$B1_{2,1} = \begin{bmatrix} 0 & 1 & 1 \\ 0 & 1 & 1 \\ 1 & 0 & 0 \end{bmatrix} B1_{2,2} = \begin{bmatrix} 1 & 1 & 0 \\ 1 & 1 & 0 \\ 0 & 0 & 1 \end{bmatrix} B1_{2,3} = \begin{bmatrix} 1 & 0 & 1 \\ 1 & 0 & 1 \\ 0 & 1 & 0 \end{bmatrix}$$

$$B1_{3,1} = \begin{bmatrix} 0 & 1 & 1 \\ 1 & 0 & 0 \\ 0 & 1 & 1 \end{bmatrix} B1_{3,2} = \begin{bmatrix} 1 & 1 & 0 \\ 0 & 0 & 1 \\ 1 & 1 & 0 \end{bmatrix} B1_{3,3} = \begin{bmatrix} 1 & 0 & 1 \\ 0 & 1 & 0 \\ 1 & 0 & 1 \end{bmatrix}$$

This first set of binary matrices corresponds to the first set of mask patterns 200 shown in FIG. 4A, where the 1's in the matrices represent the white patches in the mask patterns, and the 0's in the matrices represent the black patches in the mask patterns. Binary matrix $B1_{1,1}$ defines mask pattern 66, binary matrix $B1_{2,1}$ defines mask pattern 68, and so on.

Next, the second set of nine binary matrices is formed by replacing the −1's with 1's and the 1's with 0's in each of the basis matrices. Alternatively, this operation can be described mathematically through the following equation, producing the second set of binary matrices, $B2_{i,j}$:

$$B2_{i,j} = \left( \begin{bmatrix} 1 & 1 & 1 \\ 1 & 1 & 1 \\ 1 & 1 & 1 \end{bmatrix} - A_{i,j} \right) \cdot \frac{1}{2}$$

where $i = 1 \ldots 3, j = 1 \ldots 3$

Thus, the second set of binary matrices, $B2_{i,j}$, are:

$$B2_{1,1} = \begin{bmatrix} 0 & 1 & 1 \\ 1 & 0 & 0 \\ 1 & 0 & 0 \end{bmatrix} B2_{1,2} = \begin{bmatrix} 1 & 1 & 0 \\ 0 & 0 & 1 \\ 0 & 0 & 1 \end{bmatrix} B2_{1,3} = \begin{bmatrix} 1 & 0 & 1 \\ 0 & 1 & 0 \\ 0 & 1 & 0 \end{bmatrix}$$

$$B2_{2,1} = \begin{bmatrix} 1 & 0 & 0 \\ 1 & 0 & 0 \\ 0 & 1 & 1 \end{bmatrix} B2_{2,2} = \begin{bmatrix} 0 & 0 & 1 \\ 0 & 0 & 1 \\ 1 & 1 & 0 \end{bmatrix} B2_{2,3} = \begin{bmatrix} 0 & 1 & 0 \\ 0 & 1 & 0 \\ 1 & 0 & 1 \end{bmatrix}$$

$$B2_{3,1} = \begin{bmatrix} 1 & 0 & 0 \\ 0 & 1 & 1 \\ 1 & 0 & 0 \end{bmatrix} B2_{3,2} = \begin{bmatrix} 0 & 0 & 1 \\ 1 & 1 & 0 \\ 0 & 0 & 1 \end{bmatrix} B2_{3,3} = \begin{bmatrix} 0 & 1 & 0 \\ 1 & 0 & 1 \\ 0 & 1 & 0 \end{bmatrix}$$

This second set of binary matrices corresponds to the second set of mask patterns 300 shown in FIG. 4B, where the 1's in the matrices represent the white patches in the mask patterns, and the 0's in the matrices represent the black patches in the mask patterns. Binary matrix $B2_{1,1}$ defines mask pattern 84, binary matrix $B2_{2,1}$ defines mask pattern 86, and so on.

Figure 5:
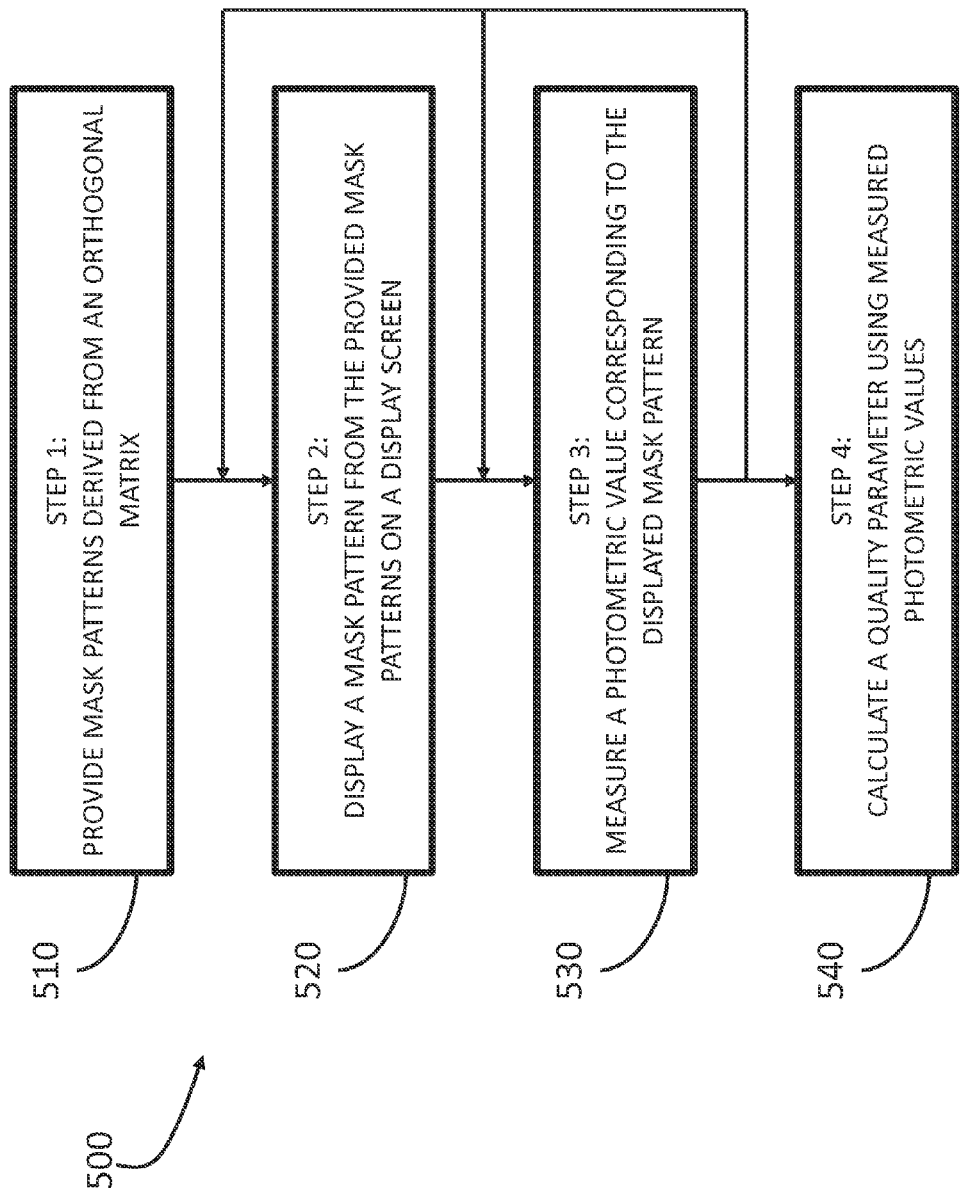
FIG. 5 shows a flowchart of a method used to measure a video screen's luminance uniformity according to some embodiments of the present invention.

FIG. 5 depicts a flowchart of a method 500 to measure a quality parameter, such as luminance uniformity, of a video display, according to some embodiments of the present invention. In a first step 510, mask patterns derived from an orthogonal matrix (as discussed above) are provided. The mask patterns are preferably derived well in advance of being displayed, and are provided in a format suitable for display on the display screen to be measured, for example, as a sequence of mask patterns in the form of a digital video file. The mask patterns may be provided by, for example, storing them on computer-readable media, or making them available for download from the internet. In a second step 520, a mask pattern from the provided set of mask patterns is displayed on a display screen. In a third step 530, a photometric value, such as luminance, is measured from the display screen using a wide-angle light sensor. The photometric value corresponds to the displayed mask pattern. Next, the displaying step 520 and measuring step 530 are repeated for each of the mask patterns in the provided set of mask patterns. In a fourth step 540, the video display quality parameter, such as luminance uniformity, is calculated using the measured photometric values.

Figure 6:
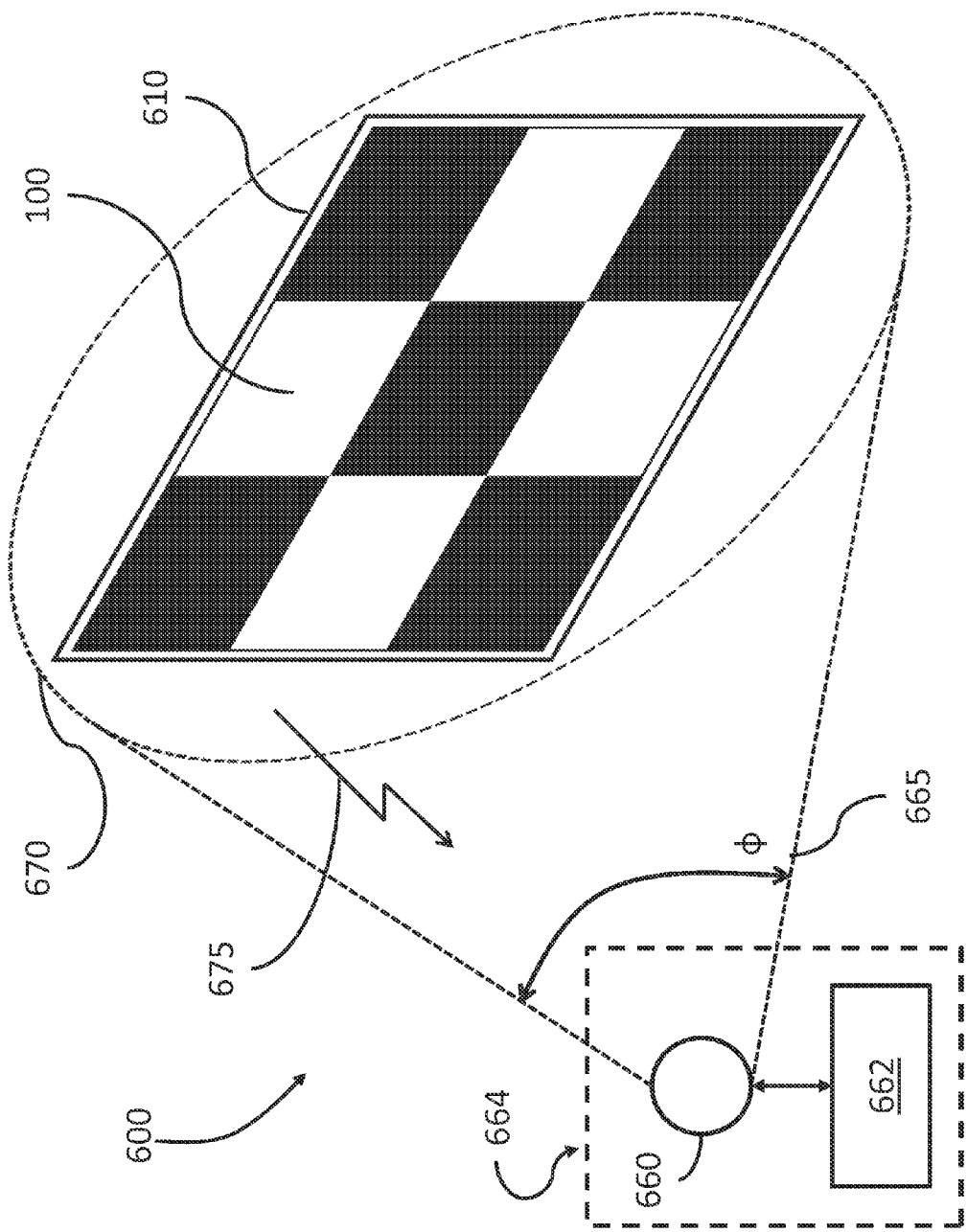
FIG. 6 illustrates an apparatus used to measure a video screen's luminance uniformity according to some embodiments of the present invention.

FIG. 6 shows a perspective view of an example of an apparatus 600 for measuring a quality parameter, such as luminance uniformity, of a video display, according to some embodiments of the present invention. A mask pattern from a set of provided mask patterns, for example, mask pattern 100, is displayed on a display screen 610. From a selected viewing location, a user (not shown) aims a wide-angle, incident light sensor 660 toward the display screen 610. Similar to discussion of FIG. 2 above, the viewing location may be selected as a typical viewer's distance from the screen, or, in the case of a cinema screen, may be selected according to the relevant measurement specification, for example, the SMPTE specification's six required seat locations. Because the light sensor 660 has a relatively wide viewing angle 665, the light sensor 660 captures the light from a relatively large area 670, including both the light produced by all patches of the displayed mask pattern 100, plus any ambient and background light 675.

The light sensor 660 measures at least one photometric value, such as luminance, from the display 610 while the mask pattern (e.g. mask pattern 100) is being displayed. As each of the remaining mask patterns in the provided sequence of mask patterns are displayed, the light sensor 660 measures at least one photometric value corresponding to each mask pattern. These photometric values may be transmitted to a processor 662, and may be recorded by the processor 662 in, for example, internal memory. When all of the mask patterns in the provided sequence of mask patterns have been displayed at least once, the processor 662 calculates a video display quality parameter, such as luminance uniformity, using the measured photometric values.

The sequence of displaying the provided set of mask patterns may be controlled manually by the user, or may be coordinated automatically by the processor 662 in communication with the light sensor 660. The sets of mask patterns provided may contain an indication or a mark, such as a pause, either between each mask pattern within the set, or at the beginning of a set. Such marks allow the processor 662 to easily automatically synchronize a measurement with the display of a mask pattern. Alternatively, the processor 662 could monitor the light sensor 660 for changes in sensor readings to determine when the displayed mask pattern changes. The light sensor 660 and the processor 662 may comprise separate devices, or they may be combined into one device 664, such as a mobile phone equipped with a camera.

The processor 662 calculates a video display quality parameter using the set of measured photometric values corresponding to the set of provided mask patterns and a matrix representation of the provided set of mask patterns. In some embodiments of the present invention, because each of the nine patches in a mask pattern are either "on" (white), or "off" (black), each patch either contributes, or does not contribute, respectively, to the total amount of light measured by the sensor. Thus, in addition to defining a mask pattern, each of the binary matrices discussed above also defines the amount of contribution (i.e. the weight) of each patch in a displayed mask pattern to the total amount of light measured by the sensor.

To mathematically represent the weight of each patch of a mask pattern, each binary matrix is rearranged into a row vector, where the first column of the binary matrix forms the first three elements of the row vector, the second column of the binary matrix forms the next three elements of the row vector, and the third column of the binary matrix forms the last three elements of the row vector. These row vectors may be referred to as "basis vectors." Thus, each set of nine binary matrices has a corresponding set of nine basis vectors. A set of basis vectors are then assembled into a corresponding "basis vector matrix." The basis vectors in a set are assembled into the rows of the basis vector matrix in the same order in which the corresponding set of mask patterns are to be displayed. That is, the basis vector corresponding to the first mask pattern to be displayed in a set of mask patterns becomes the first row of the basis vector matrix, the basis vector corresponding to the second mask pattern to be displayed becomes the second row of the basis vector matrix, and so on.

For example, the first binary matrix, $B1_{1,1}$, in the first set of binary matrices, $B1_{i,j}$, discussed above, is rearranged into a row vector (basis vector), $B1'_{1,1}$ as follows:

$$B1'_{1,1} = [1\ 0\ 0\ 0\ 1\ 1\ 0\ 1\ 1]$$

Then, after rearranging all nine of the binary matrices in the first set of binary matrices, $B1_{i,j}$, into the corresponding set of nine basis vectors, those nine basis vectors are assembled into the corresponding basis vector matrix BB1:

$$BB1 = \begin{bmatrix} B1'_{1,1} \\ B1'_{2,1} \\ B1'_{3,1} \\ B1'_{1,2} \\ B1'_{2,2} \\ B1'_{3,2} \\ B1'_{1,3} \\ B1'_{2,3} \\ B1'_{3,3} \end{bmatrix} = \begin{bmatrix} 1 & 0 & 0 & 0 & 1 & 1 & 0 & 1 & 1 \\ 0 & 0 & 1 & 1 & 1 & 0 & 1 & 1 & 0 \\ 0 & 1 & 0 & 1 & 0 & 1 & 1 & 0 & 1 \\ 0 & 1 & 1 & 0 & 1 & 1 & 1 & 0 & 0 \\ 1 & 1 & 0 & 1 & 1 & 0 & 0 & 0 & 1 \\ 1 & 0 & 1 & 1 & 0 & 1 & 0 & 1 & 0 \\ 0 & 1 & 1 & 1 & 0 & 0 & 0 & 1 & 1 \\ 1 & 1 & 0 & 0 & 0 & 1 & 1 & 1 & 0 \\ 1 & 0 & 1 & 0 & 1 & 0 & 1 & 0 & 1 \end{bmatrix}$$

Likewise, the second set of binary matrices, $B2_{i,j}$, discussed above, are rearranged into the corresponding set of basis vectors and assembled into the corresponding basis vector matrix BB2:

$$BB2 = \begin{bmatrix} B2'_{1,1} \\ B2'_{2,1} \\ B2'_{3,1} \\ B2'_{1,2} \\ B2'_{2,2} \\ B2'_{3,2} \\ B2'_{1,3} \\ B2'_{2,3} \\ B2'_{3,3} \end{bmatrix} = \begin{bmatrix} 0 & 1 & 1 & 1 & 0 & 0 & 1 & 0 & 0 \\ 1 & 1 & 0 & 0 & 0 & 1 & 0 & 0 & 1 \\ 1 & 0 & 1 & 0 & 1 & 0 & 0 & 1 & 0 \\ 1 & 0 & 0 & 1 & 0 & 0 & 0 & 1 & 1 \\ 0 & 0 & 1 & 0 & 0 & 1 & 1 & 1 & 0 \\ 0 & 1 & 0 & 0 & 1 & 0 & 1 & 0 & 1 \\ 1 & 0 & 0 & 0 & 1 & 1 & 1 & 0 & 0 \\ 0 & 0 & 1 & 1 & 1 & 0 & 0 & 0 & 1 \\ 0 & 1 & 0 & 1 & 0 & 1 & 0 & 1 & 0 \end{bmatrix}$$

In this basis vector matrix form, each row of the basis vector matrix represents the corresponding mask pattern within the corresponding mask pattern set, and each element within that row represents the contribution of the corresponding patch of that mask pattern to the total amount of light measured when that mask pattern is displayed.

Although the basis vectors are described as row vectors for the purpose of simplifying the matrix equations below, those skilled in the art will appreciate that, because the binary matrices are symmetric matrices, they could alternatively be rearranged into column vectors, and these column vectors could be assembled into the basis vector matrices.

The light sensor 660 is configured to take at least one measurement of a photometric value for each displayed mask pattern (e.g. mask pattern 100). In one embodiment of the invention, to measure luminance uniformity of a display screen, the light sensor is configured to take a measurement of wide-angle luminance (in units of foot-Lamberts or nits), or illuminance (in units of Lux) of incident light, for each displayed mask pattern. Thus, for each set of nine mask patterns, there is a corresponding set of nine luminance (or illuminance) values. As discussed above, these measured values also include any captured ambient and background light 675.

Assembling these measured photometric values into a vector (one vector of measured values for each mask pattern set), they conform to the following equation:

$$m = BB \cdot b$$

where:
m=vector of measured total values of light (including background light)
BB=basis vector matrix
b=vector of values of light for each patch Thus, to find the value of light for each of the nine patches of the display screen, the above equation can be solved for the vector b, by multiplying the inverse of the basis vector matrix times the vector of measured values:

$$b = BB^{-1} \cdot m$$

Since there are two complementary sets of mask patterns, with two corresponding sets of binary matrices, two corresponding basis vector matrices, BB1 and BB2, and two corresponding vectors of measured total light, m1 and m2, the equation above can be used to solve for two corresponding vectors of patch light values, b1 and b2:

$$b1 = BB1^{-1} \cdot m1$$

$$b2 = BB2^{-1} \cdot m2$$

As described above, since they are derived from a quasi-orthogonal reduced rank 3×3 Walsh-Hadamard matrix, the mask patterns are not orthogonal, but rather quasi-orthogonal. Since a matrix $BB^{-1}$ is the inverse of a basis vector matrix BB representing a set of mask patterns, the sum of the elements of a row of matrix $BB^{-1}$ is a constant, but non-zero value.

For example, the inverses of matrices BB1 and BB2 are:

$$BB1^{-1} = \begin{bmatrix} -0.2 & -0.2 & -0.2 & -0.2 & 0.3 & 0.3 & -0.2 & 0.3 & 0.3 \\ -0.2 & -0.2 & -0.2 & 0.3 & 0.3 & -0.2 & 0.3 & 0.3 & -0.2 \\ -0.2 & -0.2 & -0.2 & 0.3 & -0.2 & 0.3 & 0.3 & -0.2 & 0.3 \\ -0.2 & 0.3 & 0.3 & -0.2 & 0.3 & 0.3 & -0.2 & -0.2 & -0.2 \\ 0.3 & 0.3 & -0.2 & 0.3 & 0.3 & -0.2 & -0.2 & -0.2 & -0.2 \\ 0.3 & -0.2 & 0.3 & 0.3 & -0.2 & 0.3 & -0.2 & -0.2 & -0.2 \\ -0.2 & 0.3 & 0.3 & -0.2 & -0.2 & -0.2 & -0.2 & 0.3 & 0.3 \\ 0.3 & 0.3 & -0.2 & -0.2 & -0.2 & -0.2 & 0.3 & 0.3 & -0.2 \\ 0.3 & -0.2 & 0.3 & -0.2 & -0.2 & -0.2 & 0.3 & -0.2 & 0.3 \end{bmatrix}$$

$$BB2^{-1} = \begin{bmatrix} 0.25 & 0.25 & 0.25 & 0.25 & -0.25 & -0.25 & 0.25 & -0.25 & -0.25 \\ 0.25 & 0.25 & 0.25 & -0.25 & -0.25 & 0.25 & -0.25 & -0.25 & 0.25 \\ 0.25 & 0.25 & 0.25 & -0.25 & 0.25 & -0.25 & -0.25 & 0.25 & -0.25 \\ 0.25 & -0.25 & -0.25 & 0.25 & -0.25 & -0.25 & 0.25 & 0.25 & 0.25 \\ -0.25 & -0.25 & 0.25 & -0.25 & -0.25 & 0.25 & 0.25 & 0.25 & 0.25 \\ -0.25 & 0.25 & -0.25 & -0.25 & 0.25 & -0.25 & 0.25 & 0.25 & 0.25 \\ 0.25 & -0.25 & -0.25 & 0.25 & 0.25 & 0.25 & 0.25 & -0.25 & -0.25 \\ -0.25 & -0.25 & 0.25 & 0.25 & 0.25 & 0.25 & -0.25 & -0.25 & 0.25 \\ -0.25 & 0.25 & -0.25 & 0.25 & 0.25 & 0.25 & -0.25 & 0.25 & -0.25 \end{bmatrix}$$

It can be seen that $BB1^{-1}$ and $BB2^{-1}$ have constant, non-zero row element sums of one-fifth (0.2) and one-fourth (0.25), respectively. These non-zero row element sums create a small contribution of background light which the processor 662 effectively removes when calculating the desired screen quality parameter, such as luminance uniformity.

Assuming that the background light remains constant between each measurement, and letting Bge be a vector of constant background light values bge, the equations for the vectors of measured values including background light, m1 and m2, can be rewritten as:

$$m1 = BB1 \cdot bm1 + Bge$$

$$m2 = BB2 \cdot bm2 + Bge$$

These equations can be solved for the vectors bm1 and bm2, which are the desired values for determining luminance uniformity. That is, bm1 and bm2 are the patch light values excluding background light:

$$bm1 = BB1^{-1} \cdot m1 - BB1^{-1} \cdot Bge$$

$$bm2 = BB2^{-1} \cdot m2 - BB2^{-1} \cdot Bge$$

Since Bge is a vector of constant background light values, bge, the term that is the product of Bge and an inverse basis vector matrix is reduced to bge times the non-zero row element sum of the inverse basis vector matrix times a unit vector. Thus, the two equations above can be rewritten as:

$$bm1 = BB1^{-1} \cdot m1 - bge\left(\frac{4}{20}\right)u$$

$$bm2 = BB2^{-1} \cdot m2 - bge\left(\frac{5}{20}\right)u$$

where $u$ is a unit vector

Since the patch light values excluding background light should be the same for each set of mask patterns, it can be assumed that bm1=bm2. Then, substituting b1 and b2 yields:

$$b2 - b1 = \left(bge\left(\frac{5}{20}\right) - bge\left(\frac{4}{20}\right)\right)u$$

Therefore, bge, the constant scalar value of background light that is added to each measurement is:

$$bge = \left(\frac{20}{9}\right)\sum(b2 - b1)$$

Furthermore, those skilled in the art will appreciate that by averaging the two vectors of measured patch light values excluding background light, bm1 and bm2, the error in the elements of vector b of computed patch light values, is reduced. Therefore:

$$b = \frac{(bm2 + bm1)}{2}$$

$$b = \frac{\left(b2 - \left(\frac{bge}{4}\right)u + b1 - \left(\frac{bge}{5}\right)u\right)}{2}$$

$$b = \frac{b2 + b1 - bge\left(\frac{9}{20}\right)u}{2}$$

Or, simply:

$$b = \frac{b2 + b1 - \sum(b2 - b1)}{2}$$

In summary, taking the sum of the difference between the two vectors of patch light values including background light, b1 and b2, and multiplying that sum by an appropriate scale factor (twenty-ninths, in this example), gives the constant amount of background light, bge, that was captured in each measurement. By using an average of measurements to reduce measurement error, the value of background light, bge, is effectively subtracted from the vectors of patch light values, b1 and b2, by subtracting the sum of the difference of these two vectors, from their vector sum, and dividing by two.

Those skilled in the art will appreciate that if fully orthogonal mask patterns rather than quasi-orthogonal mask patterns are used, the background light, bge, is fully removed, and the equation for vector b becomes simply:

$$b = \frac{b2 + b1}{2}$$

For visual and computational convenience, the vector of computed patch values can be rearranged into a 3×3 matrix by making the first three elements of the vector the first column of the matrix, the next three elements of the vector the second column of the matrix, and the last three elements of the vector that third column of the matrix. In this matrix form, the position of an element in the matrix corresponds to the physical position of a measurement zone of the display screen. Further, this matrix can be normalized against the center element so that each element is expressed in a percentage relative to the center element. For example, a vector of patch values, b, can be rearranged into a matrix of patch values M, and then normalized into matrix M' as follows:

$$b = \begin{bmatrix} 2.5 \\ 3 \\ 3.5 \\ 2.7 \\ 3.7 \\ 2.9 \\ 3.3 \\ 2.7 \\ 2.6 \end{bmatrix}$$

$$M = \begin{bmatrix} 2.5 & 2.7 & 3.3 \\ 3 & 3.7 & 2.7 \\ 3.5 & 2.9 & 2.6 \end{bmatrix}$$

$$M' = \begin{bmatrix} 68\% & 73\% & 89\% \\ 81\% & 100\% & 73\% \\ 95\% & 78\% & 70\% \end{bmatrix}$$

The processor 662 can evaluate each element of matrix M to determine if it meets the relevant specifications, and the user can be alerted if the value does not fall within specified limits.

The preceding examples have assumed mask patterns composed of patches, where each patch is illuminated with white light to one of two intensity levels: either zero intensity (that is, the patch appears black), or full intensity (that is, the patch appears white). These mask patterns are the preferred embodiment of the present invention when the user is measuring luminance uniformity. Other embodiments of the invention are used to measure other display screen quality parameters.

Another embodiment of the present invention is used to measure a screen's chrominance (white-point) uniformity quality parameter, i.e. color-cast across the screen in both the horizontal and vertical dimensions. In this embodiment, the type of light sensor 660 used to measure light from display screen 610 is a wide-angle or incident light colorimeter. If the colorimeter 660 is capable of measuring the red, green, and blue components of light simultaneously, then the steps of the process are the same as those described above for measuring luminance uniformity, except that three photometric values are measured for each displayed mask pattern: one for the red component of light, one for the green component, and one for the blue component. Accordingly, three pairs of vectors of measured values are used to calculate three chrominance uniformity results: one for red light, one for green light, and one for blue light. Alternatively, if the colorimeter 660 is capable of measuring only one component of light at a time, then the steps of the process are the same as those described above for measuring luminance uniformity, except that the entire process is cycled three times for each sensor measurement location. In one cycle, the mask patterns used are illuminated with only red light (instead of white), thus the patterns will appear as black and red patches. In another cycle, the mask patterns used are illuminated with only green light. In a third cycle, the mask patterns used are illuminated with only blue light. Red light chrominance uniformity is calculated in the first cycle, green light chrominance uniformity is calculated in the second cycle, and blue light chrominance uniformity is calculated in the third cycle.

Another embodiment of the present invention is used to measure a screen's grayscale uniformity quality parameter, i.e. color component transfer curves (gammas) and grayscale tracking versus luminance level across the screen in both the horizontal and vertical dimensions. In this embodiment, the steps of the process are the same as those described above for measuring luminance uniformity, except that the entire process is cycled three times for each measurement location. In each cycle, the mask patterns used are illuminated with white light. In all three cycles, the first selected intensity of light is zero, that is, some patches will be black in all three cycles. The second selected intensity of light varies with each cycle. In one cycle, the second selected intensity of light is a relatively low intensity, for example, 25% of full intensity. In another cycle, the second selected intensity of light is a medium intensity, for example, 50% of full intensity. In a third cycle, the second selected intensity of light is a relatively high intensity, for example, 75% of full intensity. Thus, the mask patterns in each cycle will appear as being composed of black and gray rectangles, with the shade of gray changing between each cycle.

Another embodiment of the present invention is used to measure a screen's stereoscopic 3D (three-dimensional) crosstalk uniformity quality parameter, i.e. the amount of crosstalk from left-to-right images (L-to-R) and from right-to-left images (R-to-L) across the screen in both the horizontal and vertical dimensions. As is well known in the art, modern 3D movies are typically viewed by projecting two simultaneous streams of images onto the screen. One stream of images, intended to be viewed by the left eye, is projected through one polarizing filter. The other stream of images, intended to be viewed by the right eye, is projected through an orthogonal polarizing filter. A viewer's 3D glasses have a left-polarized lens that only allows the left-polarized images through and a right-polarized lens that only allows the right-polarized images through. Screens for 3D movies often employ a special metallized surface that is designed to maintain the orthogonal polarization of the left and right images. This surface can become damaged or dirty, which causes an increased in the stereoscopic 3D crosstalk, that is, the amount of left image that can be seen through the right lens (L-to-R crosstalk), and vice-versa (R-to-L crosstalk). The amount of L-to-R crosstalk, or R-to-L crosstalk, or both, can be non-uniform across the surface of the screen, and may also depend on viewing angle or viewing distance.

In an embodiment of the present invention used to measure stereoscopic 3D crosstalk uniformity, the steps of the process, and the composition of the mask patterns used, are the same as those described above for measuring luminance uniformity, with the following exceptions: (1) Each mask pattern is displayed twice: once as a left image and once as a right image. (2) When a mask pattern is displayed as a left image, two measurements are taken: one with a left polarizing lens placed over the light sensor 660 input, and one with a right polarizing lens placed over the light sensor 660 input. Similarly, when a mask pattern is displayed as a right image, two measurements are taken: one with a left polarizing lens placed over the light sensor 660 input, and one with a right polarizing lens placed over the light sensor 660 input. (3) The calculation step results in four matrices (corresponding to four vectors) of computed luminance values: one matrix for the left images as viewed through a left lens, one matrix for the left images as viewed through a right lens, one matrix for the right images viewed through a left lens, and one matrix for the right images as viewed through a right lens. The two matrices for the left images are compared, element-by-element, to calculate the ratio of L-to-R crosstalk, for each measurement zone of the screen. Likewise, the two matrices for the right images are compared, element-by-element, to calculate the ratio of R-to-L crosstalk, for each measurement zone of the screen.

Those skilled in the art will appreciate that techniques other than orthogonal polarization are also used to selectively present images to the left and right eyes, and that the present invention can still be used to measure stereoscopic 3D crosstalk by using a lens compatible with the technique used.

The preceding examples have assumed using mask patterns composed of nine rectangles, arranged into a 3×3 grid. These types of mask patterns are convenient to use because the nine rectangles readily map onto the nine measurement zones defined by the relevant SMTPE specification. However, those skilled in the art will recognize that other size mask patterns may also be used. For example, in other embodiments of the present invention, the mask patterns used are composed of 16 rectangles arranged into a 4×4 grid. As discussed above, these 4×4 mask patterns are derived directly from a fully orthogonal 4×4 Walsh-Hadamard matrix, resulting in a set of 16 fully orthogonal mask patterns.

Starting with the same 4×4 Walsh-Hadamard matrix H above, pairwise multiplying each column of matrix H by each row of matrix H produces a set of 16 4×4 basis matrices $A_{i,j}$, which may then be used to form the following set of 16 4×4 binary matrices $B_{i,j}$, by replacing all of the −1 elements with 0's:

$$B_{1,1} = \begin{bmatrix} 1 & 1 & 1 & 1 \\ 1 & 1 & 1 & 1 \\ 1 & 1 & 1 & 1 \\ 1 & 1 & 1 & 1 \end{bmatrix} \quad B_{1,2} = \begin{bmatrix} 1 & 1 & 0 & 0 \\ 1 & 1 & 0 & 0 \\ 1 & 1 & 0 & 0 \\ 1 & 1 & 0 & 0 \end{bmatrix}$$

$$B_{1,3} = \begin{bmatrix} 1 & 0 & 0 & 1 \\ 1 & 0 & 0 & 1 \\ 1 & 0 & 0 & 1 \\ 1 & 0 & 0 & 1 \end{bmatrix} \quad B_{1,4} = \begin{bmatrix} 1 & 0 & 1 & 0 \\ 1 & 0 & 1 & 0 \\ 1 & 0 & 1 & 0 \\ 1 & 0 & 1 & 0 \end{bmatrix}$$

$$B_{2,1} = \begin{bmatrix} 1 & 1 & 1 & 1 \\ 1 & 1 & 1 & 1 \\ 0 & 0 & 0 & 0 \\ 0 & 0 & 0 & 0 \end{bmatrix} \quad B_{2,2} = \begin{bmatrix} 1 & 1 & 0 & 0 \\ 1 & 1 & 0 & 0 \\ 0 & 0 & 1 & 1 \\ 0 & 0 & 1 & 1 \end{bmatrix}$$

$$B_{2,3} = \begin{bmatrix} 1 & 0 & 0 & 1 \\ 1 & 0 & 0 & 1 \\ 0 & 1 & 1 & 0 \\ 0 & 1 & 1 & 0 \end{bmatrix} \quad B_{2,4} = \begin{bmatrix} 1 & 0 & 1 & 0 \\ 1 & 0 & 1 & 0 \\ 0 & 1 & 0 & 1 \\ 0 & 1 & 0 & 1 \end{bmatrix}$$

$$B_{3,1} = \begin{bmatrix} 1 & 1 & 1 & 1 \\ 0 & 0 & 0 & 0 \\ 0 & 0 & 0 & 0 \\ 1 & 1 & 1 & 1 \end{bmatrix} \quad B_{3,2} = \begin{bmatrix} 1 & 1 & 0 & 0 \\ 0 & 0 & 1 & 1 \\ 0 & 0 & 1 & 1 \\ 1 & 1 & 0 & 0 \end{bmatrix}$$

$$B_{3,3} = \begin{bmatrix} 1 & 0 & 0 & 1 \\ 0 & 1 & 1 & 0 \\ 0 & 1 & 1 & 0 \\ 1 & 0 & 0 & 1 \end{bmatrix} \quad B_{3,4} = \begin{bmatrix} 1 & 0 & 1 & 0 \\ 0 & 1 & 0 & 1 \\ 0 & 1 & 0 & 1 \\ 1 & 0 & 1 & 0 \end{bmatrix}$$

$$B_{4,1} = \begin{bmatrix} 1 & 1 & 1 & 1 \\ 0 & 0 & 0 & 0 \\ 1 & 1 & 1 & 1 \\ 0 & 0 & 0 & 0 \end{bmatrix} \quad B_{4,2} = \begin{bmatrix} 1 & 1 & 0 & 0 \\ 0 & 0 & 1 & 1 \\ 1 & 1 & 0 & 0 \\ 0 & 0 & 1 & 1 \end{bmatrix}$$

$$B_{4,3} = \begin{bmatrix} 1 & 0 & 0 & 1 \\ 0 & 1 & 1 & 0 \\ 1 & 0 & 0 & 1 \\ 0 & 1 & 1 & 0 \end{bmatrix} \quad B_{4,4} = \begin{bmatrix} 1 & 0 & 1 & 0 \\ 0 & 1 & 0 & 1 \\ 1 & 0 & 1 & 0 \\ 0 & 1 & 0 & 1 \end{bmatrix}$$

Similar to the 3×3 binary matrices described above, these 16 4×4 binary matrices define a set of 16 mask patterns. Likewise, these 16 binary matrices are rearranged into a first 16×16 basis vector matrix. In this case, however, only the first row of the 16×16 basis vector matrix has a non-zero row element sum, so only the first value in a vector of 16 measured values corresponding to the 16 mask patterns includes background light value that needs to be subtracted out. The other 15 measured values already have the background light canceled out due to the other rows of the inverse of the 16×16 basis vector matrix having row element sums equal to zero. The 15 patch values corresponding to these 15 measured values (i.e. the patch values for all of the patches except the upper-left patch), are calculated by multiplying the inverse of the 16×16 basis vector matrix times the vector of 16 measured values.

To calculate the value of the upper-left patch (with the background light removed), a second set of 16 binary matrices is created by starting with the following 4×4 matrix Hr, which is the matrix H above, rotated by 180 degrees:

$$Hr = \begin{bmatrix} -1 & 1 & -1 & 1 \\ 1 & -1 & -1 & 1 \\ -1 & -1 & 1 & 1 \\ 1 & 1 & 1 & 1 \end{bmatrix}$$

Then, pairwise multiplying each column of matrix Hr by each row of matrix Hr produces a second set of 16 4×4 basis matrices, which may then be used to form the following second set of 16 4×4 binary matrices $Br_{i,j}$ by replacing all of the −1 elements with 0's:

$$Br_{1,1} = \begin{bmatrix} 1 & 0 & 1 & 0 \\ 0 & 1 & 0 & 1 \\ 1 & 0 & 1 & 0 \\ 0 & 1 & 0 & 1 \end{bmatrix} \quad Br_{1,2} = \begin{bmatrix} 0 & 1 & 1 & 0 \\ 1 & 0 & 0 & 1 \\ 0 & 1 & 1 & 0 \\ 1 & 0 & 0 & 1 \end{bmatrix}$$

$$Br_{1,3} = \begin{bmatrix} 1 & 1 & 0 & 0 \\ 0 & 0 & 1 & 1 \\ 1 & 1 & 0 & 0 \\ 0 & 0 & 1 & 1 \end{bmatrix} \quad Br_{1,4} = \begin{bmatrix} 0 & 0 & 0 & 0 \\ 1 & 1 & 1 & 1 \\ 0 & 0 & 0 & 0 \\ 1 & 1 & 1 & 1 \end{bmatrix}$$

$$Br_{2,1} = \begin{bmatrix} 0 & 1 & 0 & 1 \\ 1 & 0 & 1 & 0 \\ 1 & 0 & 1 & 0 \\ 0 & 1 & 0 & 1 \end{bmatrix} \quad Br_{2,2} = \begin{bmatrix} 1 & 0 & 0 & 1 \\ 0 & 1 & 1 & 0 \\ 0 & 1 & 1 & 0 \\ 1 & 0 & 0 & 1 \end{bmatrix}$$

$$Br_{2,3} = \begin{bmatrix} 0 & 0 & 1 & 1 \\ 1 & 1 & 0 & 0 \\ 1 & 1 & 0 & 0 \\ 0 & 0 & 1 & 1 \end{bmatrix} \quad Br_{2,4} = \begin{bmatrix} 1 & 1 & 1 & 1 \\ 0 & 0 & 0 & 0 \\ 0 & 0 & 0 & 0 \\ 1 & 1 & 1 & 1 \end{bmatrix}$$

$$Br_{3,1} = \begin{bmatrix} 1 & 0 & 1 & 0 \\ 1 & 0 & 1 & 0 \\ 0 & 1 & 0 & 1 \\ 0 & 1 & 0 & 1 \end{bmatrix} \quad Br_{3,2} = \begin{bmatrix} 0 & 1 & 1 & 0 \\ 0 & 1 & 1 & 0 \\ 1 & 0 & 0 & 1 \\ 1 & 0 & 0 & 1 \end{bmatrix}$$

$$Br_{3,3} = \begin{bmatrix} 1 & 1 & 0 & 0 \\ 1 & 1 & 0 & 0 \\ 0 & 0 & 1 & 1 \\ 0 & 0 & 1 & 1 \end{bmatrix} \quad Br_{3,4} = \begin{bmatrix} 0 & 0 & 0 & 0 \\ 0 & 0 & 0 & 0 \\ 1 & 1 & 1 & 1 \\ 1 & 1 & 1 & 1 \end{bmatrix}$$

$$Br_{4,1} = \begin{bmatrix} 0 & 1 & 0 & 1 \\ 0 & 1 & 0 & 1 \\ 0 & 1 & 0 & 1 \\ 0 & 1 & 0 & 1 \end{bmatrix} \quad Br_{4,2} = \begin{bmatrix} 1 & 0 & 0 & 1 \\ 1 & 0 & 0 & 1 \\ 1 & 0 & 0 & 1 \\ 1 & 0 & 0 & 1 \end{bmatrix}$$

$$Br_{4,3} = \begin{bmatrix} 0 & 0 & 1 & 1 \\ 0 & 0 & 1 & 1 \\ 0 & 0 & 1 & 1 \\ 0 & 0 & 1 & 1 \end{bmatrix} \quad Br_{4,4} = \begin{bmatrix} 1 & 1 & 1 & 1 \\ 1 & 1 & 1 & 1 \\ 1 & 1 & 1 & 1 \\ 1 & 1 & 1 & 1 \end{bmatrix}$$

Eight of the matrices in this second set of binary matrices, matrices $Br_{1,1}$, $Br_{1,3}$, $Br_{2,2}$, $Br_{2,4}$, $Br_{3,1}$, $Br_{3,3}$, $Br_{4,2}$, and $Br_{4,4}$, have equivalent matrices already existing within the first set of binary matrices. The mask patterns defined by these eight matrices are common between the two sets of binary matrices. However, the other eight matrices, $Br_{1,2}$, $Br_{1,4}$, $Br_{2,1}$, $Br_{2,3}$, $Br_{3,2}$, $Br_{3,4}$, $Br_{4,1}$, and $Br_{4,3}$, are unique to the second set of binary matrices. The mask patterns defined by these eight matrices are unique to the second set of binary matrices, but complementary to eight of the mask patterns in the first set. These eight complementary mask patterns are added to the set of 16 mask patterns defined by the first set of 16 binary matrices to provide a set of 24 mask patterns to be displayed on screen. The measurement process therefore results in 24 measured values.

The second set of binary matrices is rearranged into a second 16×16 basis vector matrix. Multiplying the first row of the inverse of this second basis vector matrix times a vector of 16 measured values (the eight values corresponding the eight common mask patterns plus the eight values corresponding to the eight complementary mask patterns in the second set) results in the corrected value for the first (upper-left) patch of screen. The processor 662 performs these calculations to produce 16 computed patch values.

The 16 computed patch values are arranged into a 4×4 matrix, such as, for example, the following matrix M:

$$M = \begin{bmatrix} 2.5 & 2.7 & 3.3 & 3.1 \\ 3.0 & 3.7 & 2.7 & 2.8 \\ 3.5 & 2.9 & 2.6 & 2.7 \\ 3.4 & 2.8 & 2.9 & 3.0 \end{bmatrix}$$

To determine values for the nine measurement zones defined by the relevant SMPTE specification, these 16 values are then "mapped" onto the nine defined measurement zones.

Figure 7:
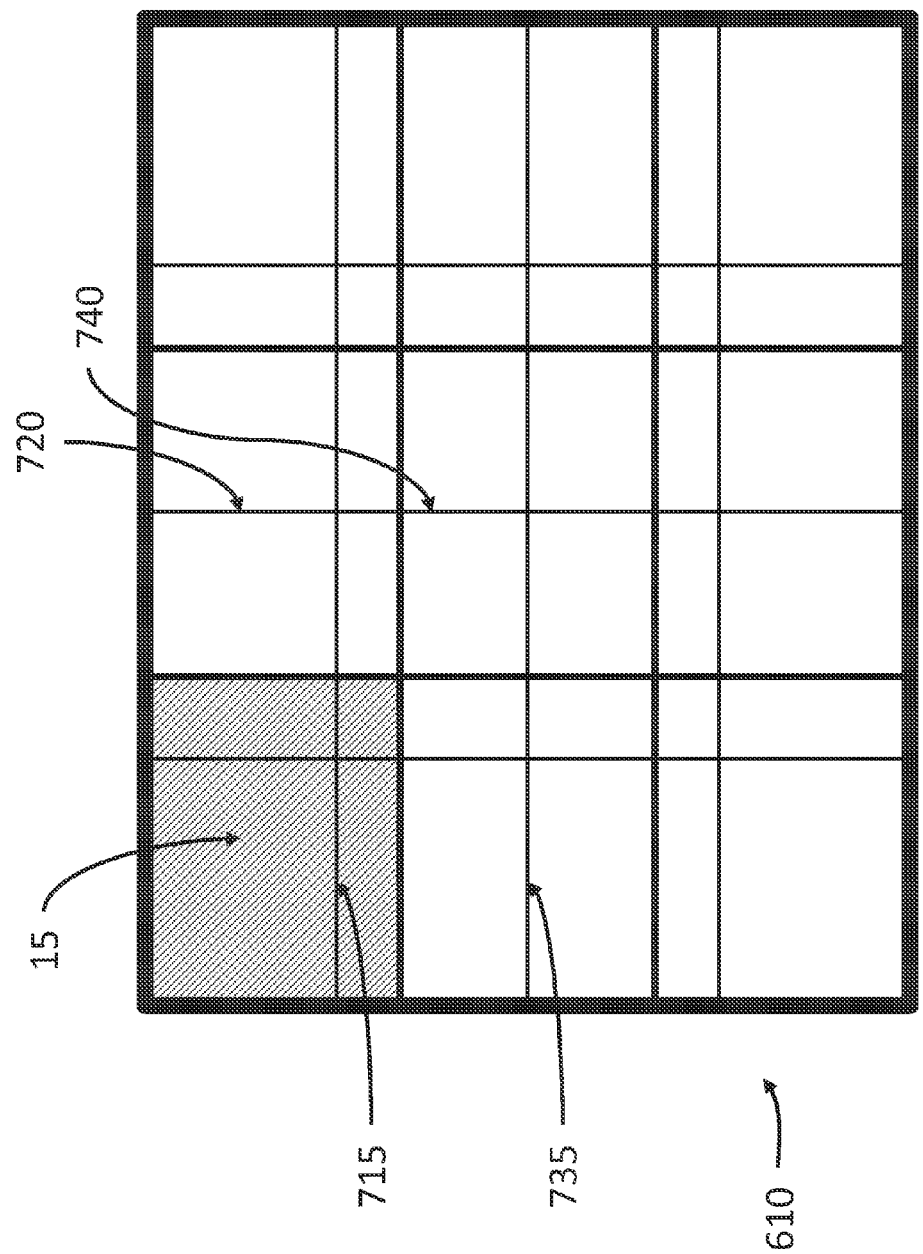
FIG. 7 illustrates, according to an embodiment of the present invention, luminance values for 16 patches of a video screen, calculated using 4×4 mask patterns, being mapped onto the 3×3 grid of nine measurement zones required by the relevant SMPTE specification.

FIG. 7 illustrates how the calculated values for 16 patches of a display screen 610 are mapped onto the nine measurement zones defined by the relevant SMPTE specification. The 16 rectangles delineated by the border of the display screen 610 and the thin lines shown in FIG. 7 define the 16 patches for which there are calculated values, corresponding to matrix M above. The position of an element in matrix M corresponds to the physical position of a patch of the display screen 610. For example, the first element of matrix M corresponds to the upper-left patch 715, having a value of 2.5. Likewise, in this example, patch 720 has a value of 2.7, patch 735 has a value of 3.0, and patch 740 has a value of 3.7. The nine measurement zones defined by the specification, delineated by the border of the display screen 610 and the medium-thick lines in FIG. 7, are overlaid on this grid of 16 patches. For example, the top-left zone 15 is shown in FIG. 7, lightly shaded for clarity. To determine a value for one of the nine measurement zones, the values for the group of four patches which overlap that measurement zone are averaged. For example, in FIG. 7, the four patches 715, 720, 735, and 740 overlap measurement zone 15. So, to determine the value for zone 15, the values for patches 715, 720, 735, and 740 are averaged (their mean is calculated). Alternatively, instead of calculating a mean of four patch values, the mapping process calculates a weighted average of the values of the four patches that overlap a zone, where the weight of a patch's value is the percentage of the patch that overlaps the zone. The processor 662 performs this mapping process.

Performing this mapping process by calculating the mean of each group of four patches on the full matrix M above would result in a 3×3 matrix N of calculated values as follows:

$$N = \begin{bmatrix} 3.0 & 3.1 & 3.0 \\ 3.3 & 3.0 & 2.7 \\ 3.2 & 2.8 & 2.8 \end{bmatrix}$$

The processor 662 can evaluate each element of matrix N to determine if it meets the relevant specifications, and the user can be alerted if the value does not fall within specified limits.

It will be appreciated from the forgoing discussion that the present invention represents a significant advance in video display quality measurement. Although specific embodiments of the invention have been illustrated and described for purposes of illustration, it will be understood that various modifications may be made without departing from the spirit and scope of the invention. Accordingly, the invention should not be limited except as by the appended claims.

What is claimed is:

1. An apparatus for measuring a video display quality parameter comprising:
a wide-angle light sensor configured to measure a plurality of photometric values from a video display, each photometric value corresponding to one of a plurality of mask patterns to be displayed sequentially on the video display, wherein each one of said mask patterns is a grid pattern derived from an orthogonal matrix; and
a processor configured to calculate the video display quality parameter using the plurality of measured photometric values.

2. The video display quality parameter measurement apparatus of claim 1 wherein the video display quality parameter is chosen from the group consisting of luminance uniformity, chrominance uniformity, grayscale uniformity, and stereoscopic 3D crosstalk uniformity.

3. The video display quality parameter measurement apparatus of claim 1 wherein the orthogonal matrix is a Walsh-Hadamard matrix.

4. The video display quality parameter measurement apparatus of claim 1 wherein the mask patterns are 3×3 grid patterns derived from a reduced rank 4×4 Walsh-Hadamard matrix, each mask pattern comprising nine equal-sized rectangular patches, half of said mask patterns having five patches illuminated at a first selected intensity level and four patches illuminated at a second selected intensity level, and half of said mask patterns having four patches illuminated at the first selected intensity level and five patches illuminated at the second selected intensity level.

5. The video display quality parameter measurement apparatus of claim 1 wherein the mask patterns are 3×3 grid patterns derived from a reduced rank 4×4 Walsh-Hadamard matrix, each mask pattern comprising nine equal-sized rectangular patches, half of said mask patterns having five patches illuminated with a first selected color of light at a first selected intensity level and four patches illuminated with a second selected color of light at a second selected intensity level, and half of said mask patterns having four patches illuminated with the first selected color of light at the first selected intensity level and five patches illuminated with the second selected color of light at the second selected intensity level.

6. The video display quality parameter measurement apparatus of claim 1 wherein the plurality of mask patterns contains an indication between each mask pattern to allow the sensor and the processor to synchronize measurement of the photometric value with display of the corresponding mask pattern.

7. The video display quality parameter measurement apparatus of claim 1 wherein the sensor comprises a reflected light meter and the measured photometric values are luminance values.

8. The video display quality parameter measurement apparatus of claim 1 wherein the sensor comprises an incident light meter and the measured photometric values are illuminance values.

9. The video display quality parameter measurement apparatus of claim 1 wherein the sensor comprises a colorimeter and the measured photometric values are chrominance values.

10. A method for measuring a video display quality parameter, comprising the steps of:
providing a plurality of mask patterns to be sequentially displayed on a video display, wherein each one of said mask patterns is a grid pattern derived from an orthogonal matrix;
measuring a plurality of photometric values from the video display using a wide-angle light sensor, each photometric value corresponding to one of the plurality of mask patterns; and
calculating the video display quality parameter using the measured photometric values.

11. The method for measuring a video display quality parameter of claim 10 wherein the mask patterns are 4×4 grid patterns derived from a 4×4 Walsh-Hadamard matrix, each mask pattern comprising 16 equal-sized rectangular patches, half of said patches illuminated at a first selected intensity level, and half of said patches illuminated at a second selected intensity level.

12. The method for measuring a video display quality parameter of claim 11 wherein the plurality of measured photometric values are averaged in a plurality of selected groups to calculate a plurality of calculated photometric values corresponding to regions of the video display.

13. The method for measuring a video display quality parameter of claim 10 wherein the mask patterns are 4×4 grid patterns derived from a 4×4 Walsh-Hadamard matrix, each mask pattern comprising 16 equal-sized rectangular patches, half of said patches illuminated with a first selected color of light at a first selected intensity level, and half of said patches illuminated with a second selected color of light at a second selected intensity level.

14. The method for measuring a video display quality parameter of claim 13 wherein the plurality of measured photometric values are averaged in a plurality of selected groups to calculate a plurality of calculated photometric values corresponding to regions of the video display.

15. The method for measuring a video display quality parameter of claim 10 wherein the mask patterns are 3×3 grid patterns derived from a reduced rank 4×4 Walsh-Hadamard matrix, each mask pattern comprising nine equal-sized rectangular patches, half of said mask patterns having five patches illuminated at a first selected intensity level and four patches illuminated at a second selected intensity level, and half of said mask patterns having four patches illuminated at the first selected intensity level and five patches illuminated at the second selected intensity level.

16. The method for measuring a video display quality parameter of claim 10 wherein the mask patterns are 3×3 grid patterns derived from a reduced rank 4×4 Walsh-Hadamard matrix, each mask pattern comprising nine equal-sized rectangular patches, half of said mask patterns having five patches illuminated with a first selected color of light at a first selected intensity level and four patches illuminated with a second selected color of light at a second selected intensity level, and half of said mask patterns having four patches illuminated with the first selected color of light at the first selected intensity level and five patches illuminated with the second selected color of light at the second selected intensity level.

17. The method for measuring a video display quality parameter of claim 10 wherein the plurality of mask patterns are organized into a first set of nine mask patterns and a second set of nine mask patterns.

18. The method for measuring a video display quality parameter of claim 17 wherein the providing step is further comprising the steps of:
removing the first row and first column of a 4×4 Walsh-Hadamard matrix to form a 3×3 quasi-orthogonal matrix;

pairwise multiplying each column of the 3×3 quasi-orthogonal matrix by each row of the 3×3 quasi-orthogonal matrix to generate a set of nine 3×3 basis matrices;

generating a first set of nine 3×3 binary matrices by replacing every element equal to negative one in each matrix in the set of nine 3×3 basis matrices with a zero;

generating a second set of nine 3×3 binary matrices by replacing every element equal to negative one in each matrix in the set of nine 3×3 basis matrices with a one, and replacing every element equal to one in each matrix in the set of nine 3×3 basis matrices with a zero;

generating the nine mask patterns in the first set of mask patterns by illuminating each patch of each mask pattern with a selected color of light at a first selected intensity level if the corresponding element of the corresponding matrix in the first set of nine 3×3 binary matrices equals zero, and at a second selected intensity level if the corresponding element of the corresponding matrix equals one; and generating the nine mask patterns in the second set of mask patterns by illuminating each patch of each mask pattern with the selected color of light at the first selected intensity level if the corresponding element of the corresponding matrix in the second set of nine 3×3 binary matrices equals zero, and at the second selected intensity level if the corresponding element of the corresponding matrix equals one.

19. The method for measuring a video display quality parameter of claim 18 wherein:
the calculated video display quality parameter is luminance uniformity;
the selected color of light is white;
the first selected intensity level is substantially zero intensity and the second selected intensity level is substantially full intensity;
the measured photometric values are luminance values and are measured using a wide-angle luminance meter; and
luminance uniformity is calculated using the measured luminance values, a first 9×9 basis vector matrix corresponding to the first set of nine 3×3 binary matrices, and a second 9×9 basis vector matrix corresponding to the second set of nine 3×3 binary matrices.

20. The method for measuring a video display quality parameter of claim 18 wherein:
the calculated video display quality parameter is luminance uniformity;
the selected color of light is white;
the first selected intensity level is substantially zero intensity and the second selected intensity level is substantially full intensity;
the measured photometric values are illuminance values and are measured using a wide-angle incident light photometer; and
luminance uniformity is calculated using the measured illuminance values, a first 9×9 basis vector matrix corresponding to the first set of nine 3×3 binary matrices, and a second 9×9 basis vector matrix corresponding to the second set of nine 3×3 binary matrices.

21. The method for measuring a video display quality parameter of claim 18 wherein:
the calculated video display quality parameter is chrominance uniformity;
the selected color of light is white;
the first selected intensity level is substantially zero intensity and the second selected intensity level is substantially full intensity;
the measured photometric values are chrominance values for each of the red, green, and blue components of light, and are measured using a wide-angle incident light colorimeter capable of measuring the red, green, and blue components of light substantially simultaneously; and
chrominance uniformity is calculated for each of the red, green, and blue components of light, using the measured chrominance values for each of the red, green, and blue components of light, a first 9×9 basis vector matrix corresponding to the first set of nine 3×3 binary matrices, and a second 9×9 basis vector matrix corresponding to the second set of nine 3×3 binary matrices.

22. The method for measuring a video display quality parameter of claim 18 wherein:
the calculated video display quality parameter is chrominance uniformity;
the measured photometric values are chrominance values, and are measured using a wide-angle incident light colorimeter configured to measure a selected color component of light;
within a first cycle comprising the providing, measuring, and calculating steps, the selected color of light is red, the first selected intensity level is substantially zero intensity, the second selected intensity level is substantially full intensity, and the colorimeter is configured to measure the red component of light;
within a second cycle comprising the providing, measuring, and calculating steps, the selected color of light is green, the first selected intensity level is substantially zero intensity, the second selected intensity level is substantially full intensity, and the colorimeter is configured to measure the green component of light;
within a third cycle comprising the providing, measuring, and calculating steps, the selected color of light is blue, the first selected intensity level is substantially zero intensity, the second selected intensity level is substantially full intensity, and the colorimeter is configured to measure the blue component of light; and
chrominance uniformity is calculated for each of the red, green, and blue components of light, using the measured chrominance values for each of the red, green, and blue components of light, a first 9×9 basis vector matrix corresponding to the first set of nine 3×3 binary matrices, and a second 9×9 basis vector matrix corresponding to the second set of nine 3×3 binary matrices.

23. The method for measuring a video display quality parameter of claim 18 wherein:
the calculated video display quality parameter is grayscale uniformity;
the measured photometric values are chrominance values and are measured using a wide-angle incident light colorimeter;
the selected color of light is white;
within a first cycle comprising the providing, measuring, and calculating steps, the first selected intensity level is substantially zero intensity, and the second selected intensity level is low intensity;
within a second cycle comprising the providing, measuring, and calculating steps, the first selected intensity level is substantially zero intensity, and the second selected intensity level is medium intensity;
within a third cycle comprising the providing, measuring, and calculating steps, the first selected intensity level is substantially zero intensity, and the second selected intensity level is high intensity; and grayscale uniformity is calculated using the measured chrominance values, a first 9×9 basis vector matrix corresponding to the first set of nine 3×3 binary matrices, and a second 9×9 basis vector matrix corresponding to the second set of nine 3×3 binary matrices.

24. The method for measuring a video display quality parameter of claim 18 wherein:

the calculated video display quality parameter is stereoscopic 3D crosstalk uniformity;

the selected color of light is white;

the first selected intensity level is substantially zero intensity and the second selected intensity level is substantially full intensity;

the measured photometric values are luminance values and are measured using a wide-angle luminance meter;

within a first cycle comprising the measuring and calculating steps, each mask pattern is displayed as a L image and the measuring step is performed twice for each displayed mask pattern, once with a L lens placed over the luminance meter input, and once with a R lens placed over the luminance meter input;

within a second cycle comprising the measuring and calculating steps, each mask pattern is displayed as a R image and the measuring step is performed twice for each displayed mask pattern, once with a L lens placed over the luminance meter input, and once with a R lens placed over the luminance meter input; and stereoscopic 3D crosstalk is calculated using the measured luminance values, a first 9×9 basis vector matrix corresponding to the first set of nine 3×3 binary matrices, and a second 9×9 basis vector matrix corresponding to the second set of nine 3×3 binary matrices.

* * * * *